(12) United States Patent
Hazra et al.

(10) Patent No.: US 6,512,130 B1
(45) Date of Patent: Jan. 28, 2003

(54) MIFEPRISTONE ANALOGUE, PROCESS FOR THE PREPARATION THEREOF AND USE THEREOF

(75) Inventors: Braja Gopal Hazra, Maharashtra (IN); Vandana Sudhir Pore, Maharashtra (IN); Padmakar Laxman Joshi, Mararashtra (IN); Sourav Basu, Maharashtra (IN); Jyotsna Singh, Uttar Pradesh (IN); Anila Dwivedi, Uttar Pradesh (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 09/656,361

(22) Filed: Sep. 6, 2000

Related U.S. Application Data

(63) Continuation-in-part of application No. 09/655,136, filed on Sep. 5, 2000, now abandoned.

(51) Int. Cl.[7] .................................................. C07J 1/00
(52) U.S. Cl. ...................................................... 552/648
(58) Field of Search ................................. 552/648, 554

(56) References Cited

PUBLICATIONS

Hazra et al., Steroids, vol. 65, pp. 157–162, Mar. 2000.*

* cited by examiner

*Primary Examiner*—Barbara P. Badio
(74) *Attorney, Agent, or Firm*—Ladas & Parry

(57) ABSTRACT

The present invention relates to the analogue, 11β-[4-(N,N-dimethylamino) phenyl]-17β-hydroxy-17α-(3-methyl-1-butynyl)-estra-4,9-dien-3-one, of the structural formula 1

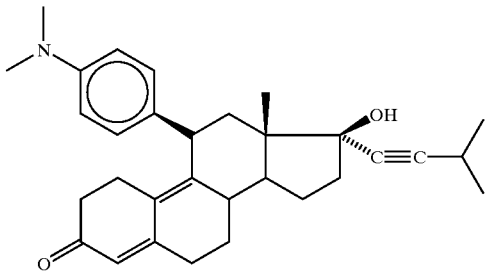

and to a method of preparation thereof.

19 Claims, 2 Drawing Sheets

Competitive binding of sample 1 to rabbit uterine progesterone receptor

Competitive binding of sample 6 and 1 to rabbit uterine progesterone receptor

MIFEPRISTONE ANALOGUE, PROCESS FOR THE PREPARATION THEREOF AND USE THEREOF

This application is a continuation-in-part of application Ser. No. 09/655,136 filed on Sept. 5, 2000 now abandoned, claims the benefit thereof and incorporates the same by reference.

FIELD OF THE INVENTION

The present invention relates to a novel analogue 11β-[4-(N,N-dimethylamino)phenyl]-17β-hydroxy-17α-(3-methyl-1-butynyl)-estra-4,9-dien-3-one of the structural formula 1,

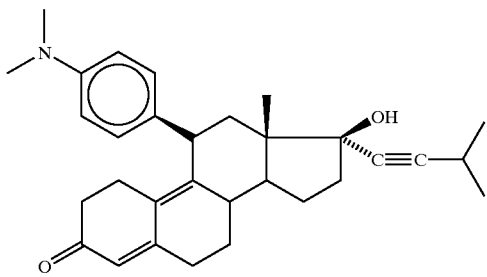

of Mifepristone of the structural formula 6

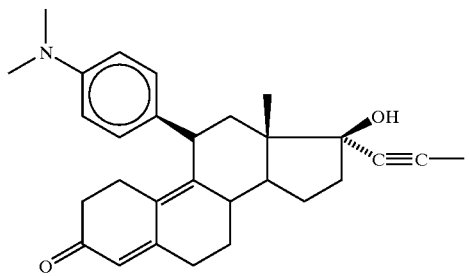

The present invention also relates to a process for the preparation of the novel analogue 11β-[4(N,N-dimethylamino)phenyl]-17β-hydroxy-17α-(3-methyl-1-butynyl)-estra-4,9-dien-3-one from estra-5(10), 9(11)-diene-3,17-dione-cyclic-3-(1,2-ethanediylacetal) of the structural formula 2.

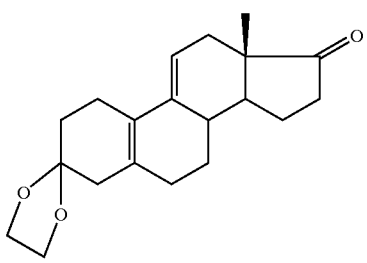

The present invention also relates to the use of the compound of formula 1 as a progesterone receptor.

BACKGROUND OF THE INVENTION

Mifeprestone (RU-486) of structural formula 6 above is an important antiprogestin that effectively and safely terminates early pregnancy and also has a wide range of other clinical features such as antiglucocorticold and anti-cancer properties. It has also shown promising activity in the treatment of estrogen dependent gynaecological disorders and hormone deficient tumours.

The compound of structural formula 2 can be prepared from (+)-estrone in seven steps. Methylation of hydroxy group at C-3 in (+)-estrone, reduction of 17-ketone to 17β-alcohol followed by Birch reduction of ring A and mild hydrolysis of the enol ether to afford estra-17β-hydroxy-5 (10)-en-3-one in four steps (Ref: Wilds, A. L. and Nelson, N. A. *J. Am. Chem. Soc.* 1953, 75, 5365–5369). This compound in another three steps, namely bromination and dehydrobrominatlon, ketalisation followed by Oppenauer oxidation yield compound having structural formula 2 (Ref: Perelman, M; Farkas, E.; Fornefield, E. J.; Kraay, R. J. and Rapala, B. T. *J. Am. Chem. Soc.* 1960, 82, 2402–2403).

U.S. Pat. No. 4,386,085 describes the synthesis of steroids of the general formula mentioned therein and exemplifies as many as 319 compounds covered by the said general formula. However, the analog of the invention is not mentioned at all in the said patent, nor is there any guidance towards the compound of formula 6 of the invention or its enhanced activity as a progesterone receptor.

OBJECTS OF THE INVENTION

It is an object of the invention to provide novel steroids with enhanced progesterone receptor activity.

It is another object of the invention to provide processes for the preparation of such novel steroids.

Accordingly, the present invention relates to a novel analog 11β-[4-(N,N-dimethylamino)phenyl]-17β-hydroxy-17α-(3-methyl-1-butynyl)-estra 4,9-dien-3-one of the structural formula 1,

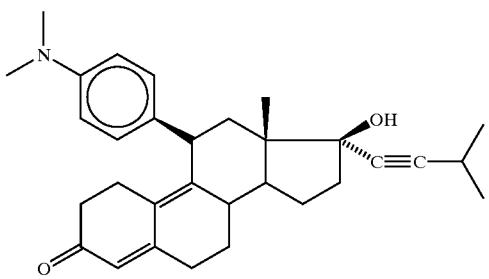

of Mifepristone of the structural formula 6.

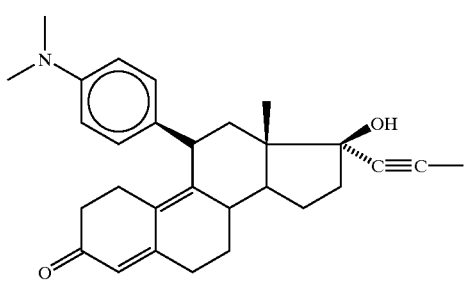

SUMMARY OF THE INVENTION

The present invention also relates to a process for the preparation of 11β-[4-(N,N-dimethylamino)phenyl]-17β- hydroxy-17α-(3-methyl-1-butynyl)-estra-4,9-dien-3-one of the structural formula 1,

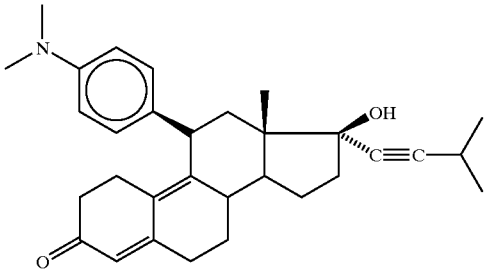

said process comprising,
i. generating 3-methyl-1-butynyl lithium in situ by the addition of butyl lithium to a solution of 1,1-dibromo-3-methyl-1-butene in an organic solvent at a temperature in the range of −50° C. to −60° C., maintaining the reaction mixture at a temperature of −45° C. to −40° C. for a period in the range of 1 to 2 hours;
ii. adding to this resultant mixture a solution of compound of the structural formula 2 at a temperature in the range of −40° C. to 0° C., stirring the reaction mixture for a period ranging between 1 to 2 hours at a temperature in the range of from −10° C. to 0° C., quenching the reaction mixture with a quenching agent, extracting the crude product having a structural formula 3 in an organic layer removing the solvent under vacuum, further purifying the crude compound 3 by any conventional method;

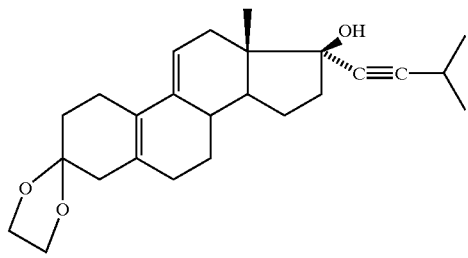

iii. converting the compound of structural formula 3 into a compound of the structural formula 4

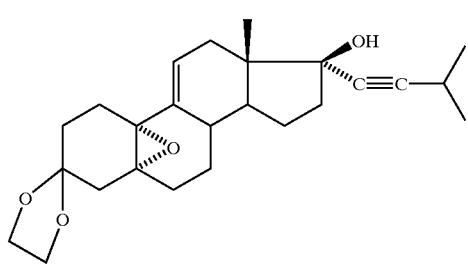

by preparing a solution of the compound having structural formula 3 in an organic solvent and adding drop wise an oxidising agent to this solution in the presence of a catalyst and buffer of pH 10 under constant stirring, maintaining the reaction temperature below 5° C.; bringing the temperature to ambient and continuing the stirring for 4 to 6 hours; extracting the crude compound 4 in a chlorinated solvent, separating the organic layer and quenching it with reducing agent, removing the solvent under vacuum and further purifying the crude product to obtain pure compound having the structural formula 4;
iv. converting the compound of formula 4 into a compound of formula 5

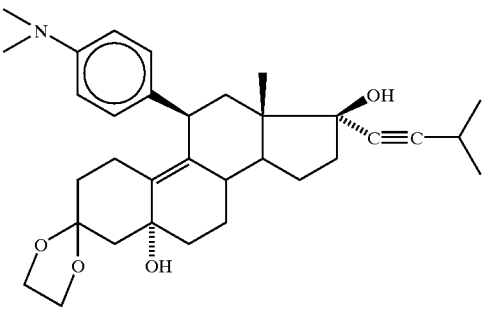

by preparing 4-(N,N-dimethylamino)phenyl magnesium bromide reagent; adding the solution of the above reagent to a mixture of a compound of formula 4 and a catalyst in an organic solvent at a temperature below −10° C., stirring the mixture for a period of 2 to 24 hours at a temperature in the range of −10° C. to 25° C., quenching the reaction mixture, extracting the compound 5 in an organic solvent, removing the solvent at a temperature below 20° C. under vacuum, further purifying the crude product to obtain the pure compound having the structural formula 5;
v. converting the compound of formula 5 to compound of formula 1 by treating the compound of formula 5 with an acid (60 to 70%) at a temperature in the range of 50° C. to 55° C. for 2 to 3 hours, neutralising with a base, extracting the crude product in organic solvent, separating the organic layer, removing the solvent under vacuum, further purifying the crude product by any conventional method to obtain the pure compound of formula 1.

In one embodiment of the invention, the organic solvent used in step i. for lithlation of 1,1-dibromo-3-methyl-1-butene is selected from the group comprising of dietylether, tetrahydrofuran, and dimethoxyethane.

In another embodiment of the invention, the quenching agent used in step ii may be selected from $NH_4Cl$ and HCl.

In another embodiment of the invention, the organic solvent used in step ii for the extraction of the compound of formula 3 may be selected from diethylether, ethyl acetate, chloroform, and dichloromethane.

In a further embodiment of the invention, the organic solvent used in step iii for preparing the solution of the compound of formula 3 may be selected from dichloromethane, chloroform and dichloroethane.

In yet another embodiment of the invention, the oxidising agent used in step iii may be selected from hydrogen peroxide, t-butyl hydroperoxide and 3-chloro perbenzoic acid.

In another embodiment of the invention, the catalyst used in step iii may be selected from hexahaloacetone, preferably hexafluoroacetone.

In still another embodiment of the invention, the reducing agent used in step iii for quenching the organic layer may be selected from sodium thiosulphate, sodium bisulphite, and sodium sulphide, preferably sodium thiosulphate.

In yet another embodiment of the invention, the catalyst used in step iv may be cuprous halide preferably cuprous iodide.

In a further embodiment of the invention, the organic used in the reaction may be selected from tetahydrofuran and diethyl ether.

In another embodiment of the invention, the organic solvent used in step iv for extracting the compound of formula 4 may be selected from the group consisting of diethyl ether, ethyl acetate, chloroform, and dichloromethane.

In another embodiment of the invention, the acid used in step v for treating the compound of formula 5 may be selected from the group consisting of acetic acid, hydrochloric acid, p-toluene sulphonic acid, and chloroacetic acid.

In a further embodiment of the invention, the base used for neutralisation in step v may be selected from sodium bicarbonate and potassium bicarbonate.

In another embodiment of the invention, the solvent used for extraction of compound of formula 1 in step v may be selected from the group consisting of diethyl ether, ethyl acetate, chloroform and dichloromethane.

BRIEF DESCRIPTION OF THE ACCOMPANYING DRAWINGS

DETAILED DESCRIPTION OF THE INVENTION

Figure 1:
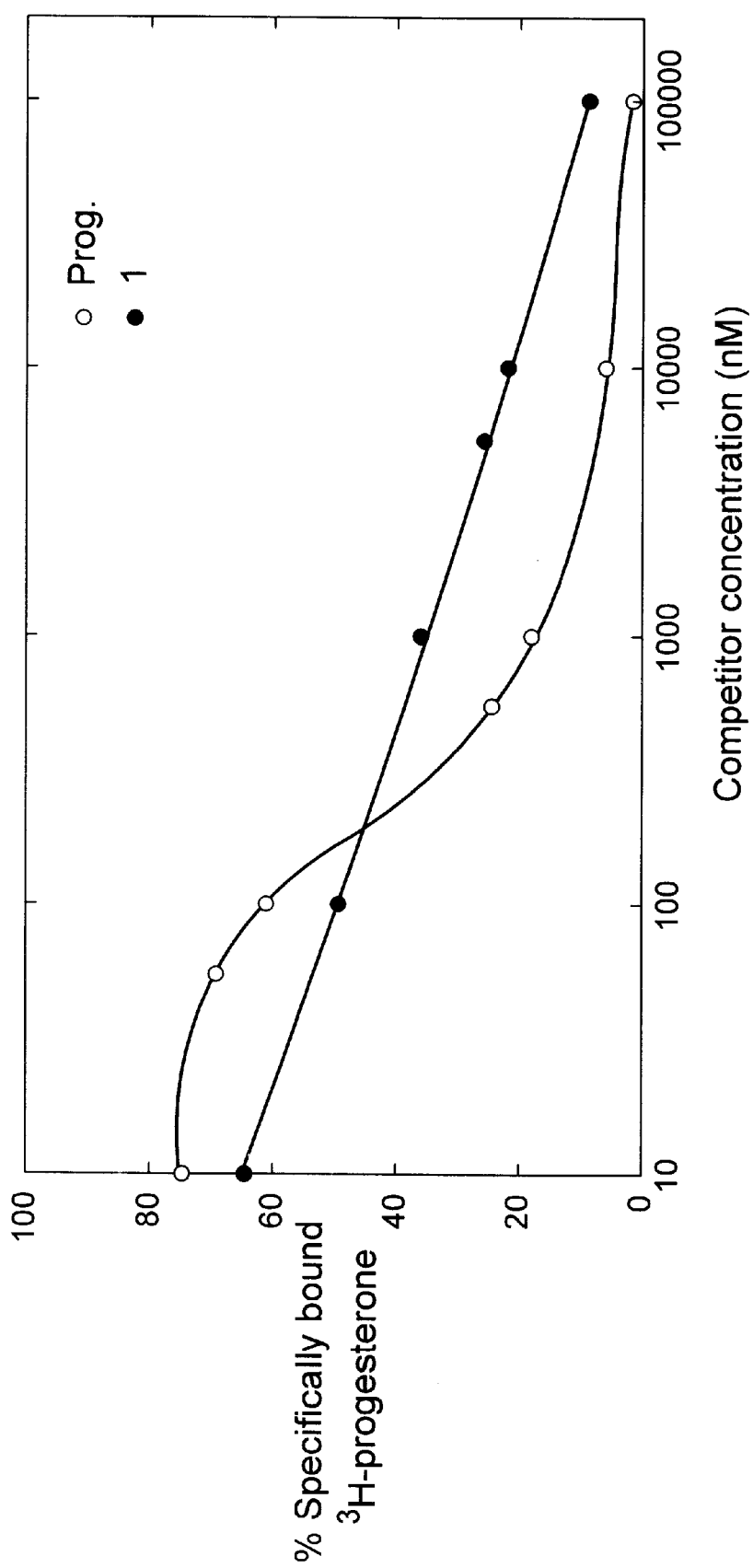
FIG. 1 is a graphical representation of the competitive binding of compound 1 to rabbit uterine progesterone receptor.

Crude products 3, 4, and 5 may be purified by column chromatography using silica gel, basic alumina, acidic alumina or neutral alumina as adsorbants and ethyl acetate, ethyl acetate-benzene, or ethyl acetate-chloroform as solvent systems. The compound of formula 1 of the invention shows marked enhancement in progesterone receptor activity. The competitive binding assay for progesterone receptors (PR) was performed using rabbit uterine cytosol and 3H progesterone (radioligand) in the presence of unlabelled cortisol at 4° C. Competitor dilutions were prepared in DMF:Tris buffer pH 7.4 (1:1). Results calculated as percent relative binding affinity for PR, revealed that the compound of structural formula 1 was the most active compound. Compound 6 showed relative binding affinity of 103%, almost equivalent to that of progesteroiie (100%) and compound 1 showed relative binding affinity of 174.65%. This shows that as compared to compound 6 (RU-486), compound 1 is more active. The activity of progesterone is taken as 100.

The following examples illustrate preferred embodiments of the invention and should not be construed as limiting the scope of the present invention.

EXAMPLE 1

In a 50 ml two necked flask equipped with a septum and a nitrogen assembly, 3-methyl-1,1-dibromobut-1-en (0.64 g, 2.8 mmol) in dry THF (15 ml) was placed under nitrogen. The solution was cooled to −78° C. and to it was added n-BuLi (2.8 ml, 5.6 mmole, 2M solution in hexane) slowly keeping the temperature −55° C. The reaction mixture was then slowly brought to −40° C. and stirred at that temperature for 2 hours. Solution of estra-5(10), 9(11)<iene-3, 17-dlonecyclic-3-(1,2-ethanediylacetal) having the structural formula 2 (0.44 g, 1.4 mmol) in THF (5 ml) was added drop wise to it and the temperature was allowed to rise slowly to 0° C. and the reaction mixture was stirred at that temperature for 2 hours. It was then quenched with ice cold saturated ammonium chloride (10 ml) solution and the mixture was extracted with ether (4×50 ml). The organic extract was washed with water (2×25 ml) and brine (2×25 ml). This was dried over anhydrous sodium sulphate and the product was isolated by removal of solvent under vacuum to afford gum (0.421 g). Column chromatographic purification over silica gel using hexane/ethyl acetate (9:1) as eluent furnished compound of the structural formula 3 as colourless foam (0.362 g, 68%) m.p. 56–58° C.; $[\alpha]^{32}$=+128.35° C. (0.79 in $CHCl_3$); —IR (nujol) γ 3410 $cm^{-1}$ (OH); —$^1$H NMR ($CDCl_3$): δ=0.85 (s, 3H, 18-$H_3$), 1.15 (d, 6H, J6, isopropyl $CH_3$), 2.46–2.75 (m, 2H, 4-$H_2$), 4.0 (s, 4H, ketal —$CH_2$), 5.65 (bd, 1H, 11-H); —MS (70 eV):m/z (%): 382 ($M^+$), 369, 332, 235, 159, 99 (100%); —$C_{25}H_{34}O_3$(382.52): calcd. C, 78.5, H 8.96; found C, 78.7, H 8.8.

The compound having the structural formula 3 (1.2 g, 3.14 mmol) was dissolved in $CH_2Cl_2$ (15 ml) and the solution was cooled to 0° C. To it $Na_2HPO_4$ (0.9 g, 0.3 mmol) was added followed by hexafluoroacetone trihydrate (0.163 g, 0.73 mmol) and 30% $H_2O_2$ (3.2 ml g, 2.85 mmol). The reaction mixture was then slowly brought to 30° C. and was stirred at that temperature for 4 hours. It was then diluted with $CH_2Cl_2$ (100 ml) and to it 10% sodium thiosulphate solution (100 ml) was added and was stirred for an additional 30 minutes. The reaction mixture was extracted with $CH_2Cl_2$ (4×25 ml), washed with water (3×25 ml), brine (2×25 ml) and was dried over anhydrous sodium sulphate. Removal of solvent under vacuum afforded a gum (0.76 g) which was chromatographed over silica gel using hexane/ethyl acetate (9:1) as eluent furnished 5, 10 β-epoxide (0.183 g, 15%), followed by 5, 10 α-epoxide of the formula 4 (0.74 g, 60%) as colourless crystalline solid, m.p. 178° C. (from hexane/ethyl acetate); $[\alpha]^{32}$=−5.6 (c 0.56 in $CHCl_3$); —IR (nujol) γ3410 $cm^{-1}$ (OH); —$^1$H NMR ($CDCl_3$); δ=0.82 (s, 3H, 18-$H_3$), 1.16 (d, 6H, J6, isopropyl $CH_3$), 2.41–2.65 (m, 2H, 4-$H_2$), 3.95 (m, 6H, ketal —$CH_2$), 6.1 (bd, 1H, 11-H); —MS (70 eV): m/z (%): 398 ($M^+$), 383 ($M^+$—$CH_3$), 337, 312, 297, 223, 141, 129, 59 (100%); —$C_{25}H_{34}O_4$ (398.55): calcd. C, 75.34, H 8.6; found C, 75.5, H8.9.

In a 50 ml two necked flask equipped with a septum and nitrogen assembly Mg (0.53 g, 22 mmol) was placed and to it 4-bromo-1N,N-dimethylaniline (4.55 g, 23 mmol) in THF (20 ml) was introduced with a syringe. The mixture was heated at 50° C. for 2 hours and during this period all Mg disappeared resulting in a yellowish solution. In another two necked flask the α-epoxide of formula 4 (0.74 g, 1.8 mmol) and CuI (0.095 g, 0.5 mmol) in THF (10 ml) were placed under nitrogen and was cooled to −5° C. to it, the performed Grignard reagent was added dropwise. The resulting reaction mixture was slowly brought to 25° C. and was stirred at that temperature for a period of 6 hours. It was then quenched with cold saturated $NH_4Cl$ solution and extracted with diethyl ether (4×25 ml). The ether extract was worked up in the usual way. Removal of solvent under reduced pressure furnished a gum (0.103 g) which was chromatographed over silica gel using ethyl acetate/hexane (1:3) to afford compound having formula 5 (0.74 g, 77%) as a solid, m.p. 103° C. from hexane/ethyl acetate); —IR (nujol) γ3460 $cm^{-1}$ (OH), 1510 (aromatic); —$^1$H NMR ($CDCl_3$): δ=0.59 (s, 3H, 18-$H_3$), 1.19 (d, 6H, J7, isopropyl $CH_3$), 1.25 (m, 1H, isopropyl —CH), 2.90 (s, 6H, N, N—$CH_3$), 3.96 (m, 4H, ketal —$CH_2$), 4.26 (d, 1H, J5, 11-H); 6.66 (d, 2H, J10, Ar—$H_2$), 7.05 (d, 2H, J10, Ar—$H_2$); —$C_{33}H_{45}NO_4$ (519.70): calcd. C, 76.26, H 8.73; found C, 76.43, H 8.6.

The solution of the hydroxy ketal of the formula 5 (0.74 g, 1.4 mmol) in 60% aqueous ACOH (15 ml) was heated at 50° C. for 2 hours. It was then cooled to 10° C. and neutralised with cold aqueous $NaHCO_3$ (25 ml). Usual work up followed by removal of solvent under vacuum afforded a yellow gum (0.087 g) which was chromatographed over silica gel using hexane/ethyl acetate (6:4) as an eluent to furnish compound of formula 1 (0.45 g, 69%), as a solid, m.p. 178° C. (from hexane/diethyl ether); $[\alpha]^{32}$=+126.25° (c, 0.48 in $CHCl_3$); —IR (nujol) γ 3415 $cm^{-1}$ (OH), 1652 (—C=O), 1517 (aromatic); $^1H$ NMR ($CDCl_3$): δ=0.56 (s, 3H, 18-$H_3$), 1.22 (d, 6H, J6, Isopropyl —$CH_3$), 2.95 (s, 6H, N, N—$CH_3$), 4.37 (d, 1H, J5, 11-H), 5.78 (s, 1H, 4-H), 6.67 (d, 2H, J8, Ar—$H_2$), 7.04 (d, 2H, J8, Ar—$H_2$), —MS (70 eV): m/z (%) 457 ($M^+$), 439 ($M^+H_2O$), 121 (100%); —$C_{31}H_{39}NO_2$ (457.63): calcd. C, 81.36, H, 8.59; found C, 81.3, H, 8.7.

EXAMPLE 2

In a 50 ml two necked flask equipped with a septum and a nitrogen assembly, 3-methyl-1,1-dibromobut-1-en (0.89 g, 3.9 mmol) in dry THF (20 ml) was placed under nitrogen. The solution was cooled to −78° C. and to it was added n-BuLi (3.9 ml, 7.8 mmole, 2M solution in hexane) slowly keeping the temperature −50° C. The reaction mixture was then slowly brought to −40° C. and stirred at that temperature for 2 hours. Solution of estra-5(10), 9(11)-diene-3, 17-dione-cyclic-3-(1,2-ethanedlylacetal) having the structural formula 2 (0.616 g, 1.96 mmol) in THF (5 ml) was added drop wise to it and the temperature was allowed to rise slowly to 0° C. and the reaction mixture was stirred at that temperature for 2 hours. It was then quenched with ice cold saturated ammonium chloride (15 ml) solution and the mixture was extracted with ether (4×50 ml). The organic extract was washed with water (2×25 ml) and brine (2×25 ml). This was dried over anhydrous sodium sulphate and the product was isolated by removal of solvent under vacuum to afford gum (0.716 g). Column chromatographic purification over silica gel using hexane/ethyl acetate (9:1) as eluent furnished compound of the structural formula 3 as colourless foam (0.484 g, 65%).

The compound having the structural formula 3 (1.8 g, 4.7 mmol) was dissolved in $CH_2Cl_2$ (20 ml) and the solution was cooled to 0° C. To it $Na_2HPO_4$ (1.68 g, 11.8 mmol) was added followed by hexafluoroacetone trihydrate (0.245 g, 1.1 mmol) and 30% $H_2O_2$ (4.6 ml, 4.3 mmol). The reaction mixture was then slowly brought to 30° C. and was stirred at that temperature for 5 hours. It was then dilated with $CH_2Cl_2$ (100 ml) and to it 10% sodium thiosulphate solution (100 ml) was added and was stirred for an additional 30 minutes. The reaction mixture was extracted with $CH_2Cl_2$ (4×25 ml), washed with water (3×25 ml), brine (2×25 ml) and was died over anhydrous sodium sulphate. Removal of solvent under vacuum afforded a gum (1.46 g) which was chromatographed over silica gel using hexane/ethyl acetate (9:1) as eluent furnished compound of the formula 4 (1.22 g, 65%) as colourless crystalline solid.

In a 50 ml two necked flask equipped with a septum and nitrogen assembly Mg (0.87 g, 36.3 mmol) was placed and to it 4-bromo-N,N-dimethylaniline (7.5 g, 37.5 mmol) in THF (20 ml) was introduced with a syringe. The mixture was heated at 45° C. for 2 hours and during this period all Mg disappeared resulting in a yellowish solution. In another two necked flask the α-epoxide of formula 4 (1.22 g, 3.07 mmol) and CuI (0.157 g, 0.82 mmol) in THF (15 ml) were placed under nitrogen and was cooled to −5° C. To it, the performed Grignard reagent was added dropwise. The resulting reaction mixture was slowly brought to 25° C. and was stirred at that temperature for a period of 6 hours. It was then quenched with cold saturated $NH_4Cl$ solution and extracted with diethyl ether (4×25 ml). The ether extract was worked up in the usual way. Removal of solvent under reduced pressure furnished a gum (1.48 g) which was chromatographed over silica gel to afford compound having formula 5 (1.36 g, 85%) as a solid.

The solution of the hydroxy ketal of the formula 5 (1.36 9, 2.6 mmol) in 65% aqueous AcOH (20 ml) was heated at 55° C. for 2 hours. It was then cooled to 10° C. and neutrallsed with cold aqueous $NaHCO_3$ (25 ml). Usual work up followed by removal of solvent under vacuum afforded a yellow gum (0.087 g) which was chromatographed over silica gel using hexane/ethyl acetate (6:4) as an eluent to furnish compound of formula 1 (0.932 g, 78%), as a solid.

EXAMPLE 3

In a 25 ml two necked flask equipped with a septum and a nitrogen assembly, 3-methyl-1,1-dibromobut-1-en (0.15 g, 0.66 mmol) in dry THF (5 ml) was placed under nitrogen. The solution was cooled to −78° C. and to it was added n-BuLi (0.66 ml, 1.33 mmole, 2M solution in hexane) slowly keeping the temperature −55° C. The reaction mixture was then slowly brought to −40° C. and stirred at that temperature for 2 hours. Solution of estra-5(10), 9(11)diene-3, 17dione-cyclic-3-(1,2ethanediylacetal) having the structural formula 2 (0.105 g, 0.33 mmol) in THF (3 ml) was added drop wise to it and the temperature was allowed to rise slowly to 0° C. and the reaction mixture was stirred at that temperature for 2 hours. It was then quenched with ice cold saturated ammonium chloride (5 ml) solution and the mixture was extracted with ether (4×50 ml). The organic extract was washed with water (2×25 ml) and brine (2×25 ml). This was dried over anhydrous sodium sulphate and the product was isolated by removal of solvent under vacuum to afford gum (0.112 g). Column chromatographic purification over silica gel using hexane/ethyl acetate (9:1) as eluent furnished compound of the structural formula 3 as colourless foam (0.09 g, 71%).

The compound having the structural formula 3 (1.5 g, 3.93 mmol) was dissolved in $CH_2Cl_2$ (20 ml) and the solution was cooled to 0° C. To it $Na_2HPO_4$ (1.4 g, 9.86 mmol) was added followed by hexafluoroacetone trihydrate (0.204 g, 0.93 mmol) and 30% $H_2O_2$ (4.0 ml, 3.56 mmol). The reaction mixture was then slowly brought to 25° C. and was stirred at that temperature for 3 hours. It was then diluted with $CH_2Cl_2$ (100 ml) and to it 10% sodium thiosulphate solution (100 ml) was added and was stirred for an additional 30 minutes. The reaction mixture was extracted with $CH_2Cl_2$ (4×25 ml), washed with water (3×25 ml), brine (2×25 ml) and was dried over anhydrous sodium sulphate. Removal of solvent under vacuum afforded a gum (1.2 g) which was chromatographed over silica gel using hexane/ethyl acetate (9:1) as eluent furnished compound of the formula 4 (0.95 g, 61%) as colourless crystalline solid.

In a 50 ml two necked flask equipped with a septum and nitrogen assembly Mg (0.68 g, 28.3 mmol) was placed and to it 4-bromo-N,N-dimethylaniline (5.84 g, 29.05 mmol) in THF (30 ml) was introduced with a syringe. The mixture was heated at 50° C. for 2 hours and during this period all Mg disappeared resulting in a yellowish solution. In another two necked flask the α-epoxide of formula 4 (0.95 g, 2.39 mmol) and CuI (0.122 g, 0.638 mmol) in THF (10 ml) were placed under nitrogen and was cooled to −5° C. to it, the performed Grignard reagent was added dropwise. The resulting reaction mixture was slowly brought to 25° C. and was stirred at that temperature for a period of 24 hours. It was then quenched with cold saturated NH₄Cl solution and extracted with diethyl ether (4×25ml). The ether extract was worked up in the usual way. Removal of solvent under vacuum furnished a gum (1.2 g) which was chromatographed over silica gel to afford compound having formula 5 (1.02 g, 82%) as a solid.

The solution of the hydroxy ketal of the formula 5 (1.02 g, 1.96 mmol) in 70% aqueous AcOH (15 ml) was heated at 50° C. for 2 hours. It was then cooled to 10° C. and neutralised with cold aqueous NaHCO₃ (25 ml). Usual work up followed by removal of solvent under vacuum afforded a yellow gum (0.85 g) which was chromatographed over silica gel using hexane/ethyl acetate (6:4) as an eluent to furnish compound of formula 1 (0.67 g, 75%) as a solid.

EXAMPLE 4

This example illustrates the progesterone receptor activity of the compound of the present invention.

PHARMACOLOGICAL STUDIES

Progesterone Receptor of the Uterus of a Rabbit

Animals. Immature rabbits weighing about 1 kg were administered 100 μg estradioldipropionate intramuscularly for four days and were sacrificed on the fifth day. Uteri were removed, washed with ice cold saline and weighed. Uteri were homogenised in four volumes of 50 mM Tris buffer, pH 7.4 containing 1 mM EDTA, 12 mM monothioglycerol and 10% glycerol (v/v) at 2° C. using polytron PT-10 homoniser.

Preparation of Cytosol

The homogenate was ultracentrifuged at 105000×g for 60 minutes at 4° C. The resultant supernatant (cytosol) was treated with equal volume of dextran coated charcoal (0.5% charcoal and 0.05% dextran in TEMG buffer) for 30 minutes with occasional stirring at 0° C. DCC treated cytosol was used for binding assay.

Binding Assay

Prior to the assay, cytosol was Incubated with 1 μM unlabelled cortisol for 30 minutes at 0° C. Aliquots of the cytosol were incubated at 4° C. for 20 hours with a constant concentration of ³H-progesterone (8×10⁻⁹ M) in the absence or presence of increasing concentration (1 to 10000×10⁻⁹ M) of either unlabelled progesteroine or test compounds. ³H-progesterone bound was measured for each incubate by the technique of charcoal adsorption.

Calculation of Relative Binding Affinity

Figure 2:
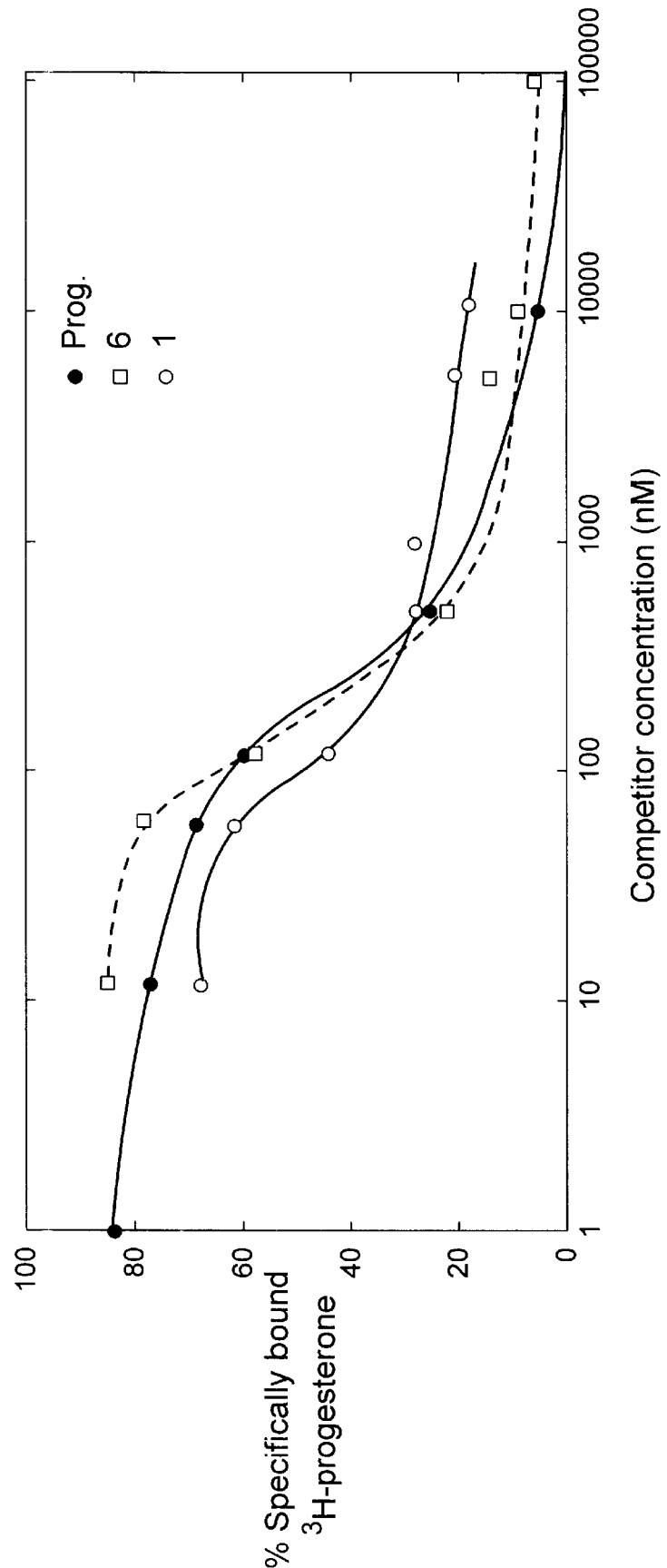
FIG. 2 is a graphical representation of the competitive binding of both compounds 6 and 1 to rabbit uterine progesterone receptor.

Calculation of relative binding affinity of test compounds was done by plotting the curves between the percentage of bound titrated progesterone as a function of the iogarithm of the unlabelled progesterone concentration and as a function of logarithm of the concentration of unlabelled test compounds (FIGS. 1 and 2). Relative binding affinity is calculated by determining the ratio of concentration of unlabelled progesterone required for 50% inhibition of specific ³H-P binding and the concentration of the unlabelled competitor test compound required for 50% inhibition of specific ³H-P binding. The figure obtained is multiplied by hundred. The results are provided below in Table I.

TABLE I

| S. No. | Compound No. | Relative binding affinity (%) |
|--------|--------------|-------------------------------|
| 1 | 6 | 103.44 |
| 2 | 1 | 174.65 |
| 3 | Progesterone | 100 |

The above results show that the tested compound having the structural formula 1 possesses a remarkable affinity for progesterone receptors. These results lead to the conclusion that the products present an agonistic or antagonistic activity to progesterone receptors.

We claim:
1. 11β-[4-(N,N-dimethylamino)phenyl]-17β-hydroxy-17α-(3-mothyl-1-butynyl)-estra-4,9-dien-3-one of the structural formula 1

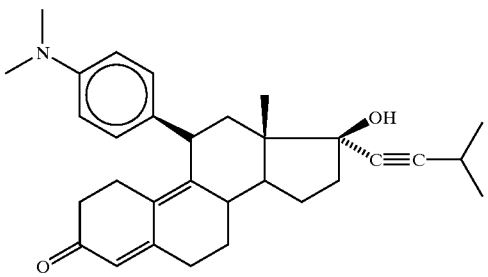

2. A process for the preparation of 11β-[4-(N,N-dimethylamino)phenyl]-17β-hydroxy-17α-(3-methyl-1-butynyl)-estra-4,9-dien-3-one of the structural formula 1 possessing enhanced binding affinity for progesterone receptors,

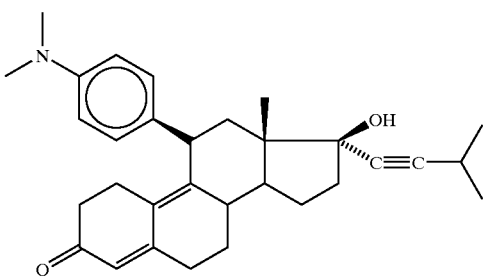

said process comprising, i. generating 3-methyl-1-butynyl lithium in situ by the addition of butyl lithium to a solution of 1,1-dibromo-3-methyl-1-butene in an organic solvent at a temperature in the range of −50° C. to −60° C., maintaining reaction mixture at a temperature of −40° C. for a period in the range of 1 to 2 hours;

ii. adding to this resultant mixture a solution of compound of structural formula 2

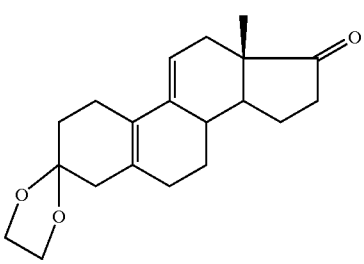

2

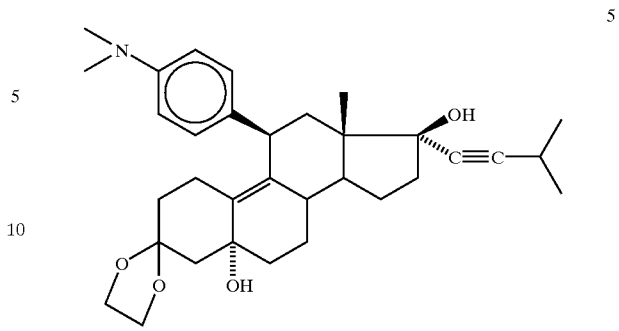

5 at a temperature in the range of −40° C. to 0° C., stirring the reaction mixture for a period ranging between 1 to 2 hours at a temperature in the range of from −10° C. to 0° C., quenching the reaction mixture with a quenching agent, extracting the crude product having a structural formula 3 with an organic solvent in an organic layer removing the solvent under vacuum, further purifying the crude compound 3 by any conventional method

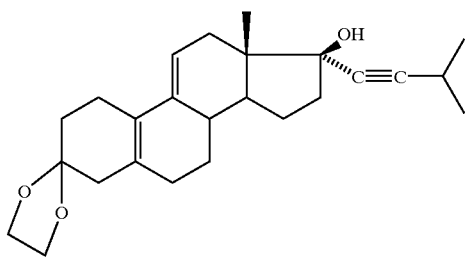

3 iii. converting the compound of structural formula 3 into a compound of the structural formula 4

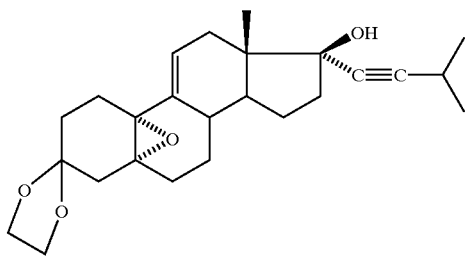

4 by preparing a solution of the compound having structural formula 3 in an organic solvent and adding dropwise an oxidising agent to this solution in the presence of a catalyst and buffer of pH 10 under constant stirring, maintaining the reaction temperature below 5° C.; bringing the temperature to ambient and continuing the stirring for 4 to 6 hours; extracting the crude compound 4 in a chlorinated solvent, separating the organic layer and quenching it with reducing agent, removing the solvent under vacuum and further purifying the crude product to obtain pure compound having the structural formula 4;

iv. converting the compound of formula 4 into a compound of formula 5 by preparing 4-(N,N-dimethylamino)phenyl magnesium bromide reagent, said reagent prepared by mixing 4-bromo-N,N-dimethylaniline with Mg and heating the mixture; adding the solution of the magnesium bromide reagent to a mixture of compound of formula 4 and a catalyst in an organic solvent at a temperature below −10° C., stirring the mixture for a period of 2 to 24 hours at a temperature in the range of −10° C. to 25° C., quenching the reaction mixture, extracting the compound 5 in an organic solvent removing the solvent at a temperature below 20° C. under vacuum, further purifying the crude product to obtain the pure compound having the structural formula 5;

v. converting the compound of structural formula 5 to compound of structural formula 1 by treating the compound of structural formula 5 with an acid (60 to 70%) at a temperature in the range of 50° C. to 55° C. for 2 to 3 hours, neutralising with a base, extracting the crude product in organic solvent, separating the organic layer, removing the solvent under vacuum, further purifying the crude product by any conventional method to obtain the pure compound of formula 1.

3. A process as claimed in claim 2 wherein the organic solvent used in step i, for lithiation of 1,1-dibromo-3-methyl-1-butene is selected from the group comprising of diethylether, tetrahydrofuran, and dimethoxyethane.

4. A process as claimed in claim 2 wherein the quenching agent used in step ii is selected from $NH_4Cl$ and HCl.

5. A process as claimed in claim 2 wherein the organic solvent used in step ii for the extraction of the compound of formula 3 is selected from the group consisting of diethylether, ethyl acetate, chloroform, and dichloromethane.

6. A process as claimed in claim 2 wherein the organic solvent used in step iii for preparing the solution of the compound of formula 3 is selected from the group consisting of dichloromethane, chloroform, and dichloroethane.

7. A process as claimed in claim 2 wherein the oxidising agent used in step iii is selected from the group consisting of hydrogen peroxide, t-butyl hydroperoxide and 3-chloro perbenzoic acid.

8. A process as claimed in claim 2 wherein the catalyst used in step iii comprises a hexahaloacetone.

9. A process as claimed in claim 8 wherein the catalyst used in step iii is hexafluoroacetone.

10. A process as claimed in claim 2 wherein the reducing agent used in step iii for quenching the organic layer is selected from the group consisting of sodium thiosulphate, sodium bisulphite, and sodium sulphide.

11. A process as claimed in claim 10 wherein the reducing agent used in step iii for quenching the organic layer is sodium thiosulphate.

12. A process as claimed in claim 2 wherein the catalyst used in step iv is a cuprous halide.

13. A process as claimed in claim 12 wherein the catalyst used in step iv is cuprous iodide.

14. A process as claimed in claim 2 wherein the organic solvent used in the reaction in step iv is selected from tetrahydrofuran and diethyl ether.

15. A process as claimed in claim 2 wherein the organic solvent used in step iv for extracting the compound of formula 4 is selected from the group consisting of diethyl ether, ethyl acetate, chloroform, and dichloromethane.

16. A process as claimed in claim 2 wherein the acid used in step v for treating the compound of formula 5 is selected from the group consisting of acetic acid, hydrochloric acid, p-toluene, sulphonic acid, and chloroacetic acid.

17. A process as claimed in claim 2 wherein the base used for neutralisation in step v is selected from sodium bicarbonate and potassium bicarbonate.

18. A process as claimed in claim 2 wherein the solvent used for extraction of compound of formula 1 in step v is selected from the group consisting of diethyl ether, ethyl acetate, chloroform and dichloromethane.

19. A method for binding to a progesterone receptor comprising administering a compound of formula 1

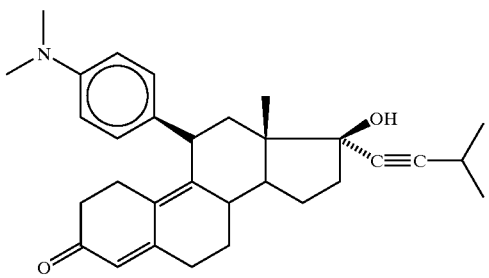

in an amount effective to bind to a progestrone receptor.

* * * * *